(12) United States Patent
Perez et al.

(10) Patent No.: US 12,402,958 B2
(45) Date of Patent: Sep. 2, 2025

(54) PATELLA TRACKING

(71) Applicant: Mako Surgical Corp., Weston, FL (US)

(72) Inventors: Daniel Antonio Perez, Miami, FL (US); Daniel Rudolf Scholl, Andover, NJ (US); Gokce Yildirim, Weehawken, NJ (US); Alvin Perez, Ringwood, NJ (US); Alex Mclachlan, Hoboken, NJ (US); Zenan Zhang, Weston, FL (US); Geoffrey Westrich, New York, NY (US)

(73) Assignee: Mako Surgical Corp., Weston, FL (US)

( * ) Notice: Subject to any disclaimer, the term of this patent is extended or adjusted under 35 U.S.C. 154(b) by 0 days.

(21) Appl. No.: 18/591,956

(22) Filed: Feb. 29, 2024

(65) Prior Publication Data

US 2024/0277419 A1  Aug. 22, 2024

Related U.S. Application Data

(63) Continuation of application No. 17/975,117, filed on Oct. 27, 2022, now Pat. No. 11,944,393, which is a
(Continued)

(51) Int. Cl.
 *A61B 34/20* (2016.01)
 *A61B 17/17* (2006.01)
(Continued)

(52) U.S. Cl.
 CPC .......... *A61B 34/20* (2016.02); *A61B 17/1767* (2013.01); *A61B 34/10* (2016.02);
(Continued)

(58) Field of Classification Search
 CPC . A61B 17/155; A61B 17/158; A61B 17/1767; A61B 2034/102;
(Continued)

(56) References Cited

U.S. PATENT DOCUMENTS

| 4,309,778 A | 1/1982 | Buechel et al. |
| 4,340,978 A | 7/1982 | Buechel et al. |

(Continued)

FOREIGN PATENT DOCUMENTS

| DE | 10309500 A1 | 9/2004 |
| EP | 0497955 A1 | 8/1992 |

(Continued)

*Primary Examiner* — Mark D Remaly
(74) *Attorney, Agent, or Firm* — Lerner David LLP

(57) ABSTRACT

Disclosed herein are a surgical system for patella tracking and a method for selecting a properly-sized patellar implant utilizing the same. The surgical system may include first and second trackers and a patellar tracking system. The first tracker may be configured to contact an unresected or a resected patella, and the second tracker may be configured to contact a bone. The patellar tracking system may be configured to track the first and second trackers during patellar flexion and extension to generate patellar range of motion and patellar trial range of motion. A method for selecting a patellar implant may utilize the first and second trackers and the patellar tracking system.

20 Claims, 12 Drawing Sheets

Related U.S. Application Data continuation of application No. 16/447,364, filed on Jun. 20, 2019, now Pat. No. 11,510,737.

(60) Provisional application No. 62/687,875, filed on Jun. 21, 2018.

(51) Int. Cl.
*A61B 34/10* (2016.01)
*A61B 17/15* (2006.01)
*A61B 34/30* (2016.01)
*A61B 90/00* (2016.01)

(52) U.S. Cl.
CPC ....... *A61B 17/155* (2013.01); *A61B 2034/102* (2016.02); *A61B 2034/105* (2016.02); *A61B 2034/108* (2016.02); *A61B 2034/2057* (2016.02); *A61B 34/30* (2016.02); *A61B 90/37* (2016.02)

(58) Field of Classification Search
CPC ........ A61B 2034/105; A61B 2034/108; A61B 2034/2055; A61B 2034/2057; A61B 34/10; A61B 34/20; A61B 34/30; A61B 90/37; A61F 2002/3881; A61F 2002/4668; A61F 2/3877; A61F 2/4657; A61F 2/4684

See application file for complete search history.

(56) References Cited

U.S. PATENT DOCUMENTS

| | | | |
|---|---|---|---|
| 4,470,158 | A | 9/1984 | Pappas et al. |
| 5,246,460 | A | 9/1993 | Goodfellow et al. |
| 6,855,150 | B1 | 2/2005 | Linehan |
| 6,923,817 | B2 | 8/2005 | Carson et al. |
| 7,337,007 | B2 | 2/2008 | Nathan et al. |
| 7,840,253 | B2 | 11/2010 | Tremblay et al. |
| 7,892,236 | B1 | 2/2011 | Bonutti |
| 8,165,659 | B2 | 4/2012 | Sheffer et al. |
| 8,361,160 | B2 | 1/2013 | Haechler et al. |
| 8,444,564 | B2 | 5/2013 | Mahfouz et al. |
| 8,571,637 | B2 | 10/2013 | Sheffer et al. |
| 8,845,645 | B2 | 9/2014 | Wilkinson et al. |
| 9,050,132 | B2 | 6/2015 | Lavallee |
| 9,125,746 | B2 | 9/2015 | Clifford et al. |
| 9,220,510 | B2 | 12/2015 | Cheal et al. |
| 9,220,571 | B2 | 12/2015 | Lavallee |
| 9,452,022 | B2 | 9/2016 | McIntosh et al. |
| 9,452,023 | B2 | 9/2016 | Boillot et al. |
| 2002/0133162 | A1 | 9/2002 | Axelson et al. |
| 2005/0171545 | A1 | 8/2005 | Walsh et al. |
| 2005/0251026 | A1 | 11/2005 | Stone |
| 2005/0277832 | A1 | 12/2005 | Foley et al. |
| 2006/0052792 | A1 | 3/2006 | Boettiger et al. |
| 2007/0016008 | A1 | 1/2007 | Schoenefeld |
| 2007/0233121 | A1 | 10/2007 | Carson et al. |
| 2008/0183108 | A1 | 7/2008 | Huber et al. |
| 2008/0208081 | A1 | 8/2008 | Murphy et al. |
| 2008/0249394 | A1 | 10/2008 | Giori et al. |
| 2009/0076371 | A1 | 3/2009 | Lang et al. |
| 2009/0281428 | A1 | 11/2009 | Kammerzell et al. |
| 2010/0010506 | A1 | 1/2010 | Murphy |
| 2011/0071528 | A1 | 3/2011 | Carson |
| 2011/0071529 | A1 | 3/2011 | Carson |
| 2011/0071530 | A1 | 3/2011 | Carson |
| 2011/0071531 | A1 | 3/2011 | Carson |
| 2014/0276943 | A1 | 9/2014 | Bowling et al. |
| 2014/0277526 | A1 | 9/2014 | Stein et al. |
| 2014/0277542 | A1 | 9/2014 | Stein et al. |
| 2014/0364807 | A1 | 12/2014 | Couture et al. |
| 2015/0157416 | A1 | 6/2015 | Andersson |
| 2015/0193591 | A1 | 7/2015 | Lavallee et al. |
| 2015/0202022 | A1 | 7/2015 | Branch et al. |
| 2015/0313546 | A1 | 11/2015 | Revie et al. |
| 2015/0313727 | A1 | 11/2015 | Waite et al. |
| 2015/0327947 | A1 | 11/2015 | Schoenefeld |
| 2016/0007909 | A1 | 1/2016 | Singh et al. |
| 2016/0022374 | A1 | 1/2016 | Haider et al. |
| 2016/0058519 | A1 | 3/2016 | Herr |
| 2016/0081758 | A1 | 3/2016 | Bonutti |
| 2016/0081808 | A1 | 3/2016 | McCombs |
| 2016/0106515 | A1 | 4/2016 | Kling et al. |
| 2016/0106554 | A1 | 4/2016 | Lavallee |
| 2016/0120610 | A1 | 5/2016 | Wu |
| 2016/0157940 | A1 | 6/2016 | Stein et al. |
| 2016/0206376 | A1 | 7/2016 | Haider et al. |
| 2016/0206377 | A1 | 7/2016 | Cheal et al. |
| 2016/0217268 | A1 | 7/2016 | Otto et al. |
| 2016/0220312 | A1 | 8/2016 | Mahfouz |
| 2016/0220438 | A1 | 8/2016 | Walsh et al. |
| 2016/0242858 | A1 | 8/2016 | Moctezuma de la Barrera et al. |
| 2016/0270696 | A1 | 9/2016 | Lang et al. |
| 2016/0270859 | A1 | 9/2016 | Park et al. |
| 2016/0278943 | A1 | 9/2016 | van der Walt et al. |
| 2016/0324646 | A1 | 11/2016 | Carignan et al. |
| 2016/0331465 | A1 | 11/2016 | Kim et al. |
| 2016/0338649 | A1 | 11/2016 | Branch et al. |
| 2016/0354153 | A1 | 12/2016 | Hodgson et al. |
| 2016/0361101 | A1 | 12/2016 | Moctezuma de la Barrera et al. |
| 2017/0000614 | A1 | 1/2017 | Mahfouz |
| 2017/0000615 | A1 | 1/2017 | Mahfouz |
| 2017/0007408 | A1 | 1/2017 | Fitz et al. |
| 2017/0027701 | A1 | 2/2017 | Mahfouz |
| 2017/0042557 | A1 | 2/2017 | Plaskos et al. |
| 2017/0042622 | A1 | 2/2017 | Yang et al. |
| 2017/0056022 | A1 | 3/2017 | Cheal et al. |

FOREIGN PATENT DOCUMENTS

| | | |
|---|---|---|
| EP | 0676182 A1 | 10/1995 |
| EP | 1582184 A1 | 10/2005 |
| FR | 2700260 A1 | 7/1994 |
| GB | 2247407 A | 3/1992 |

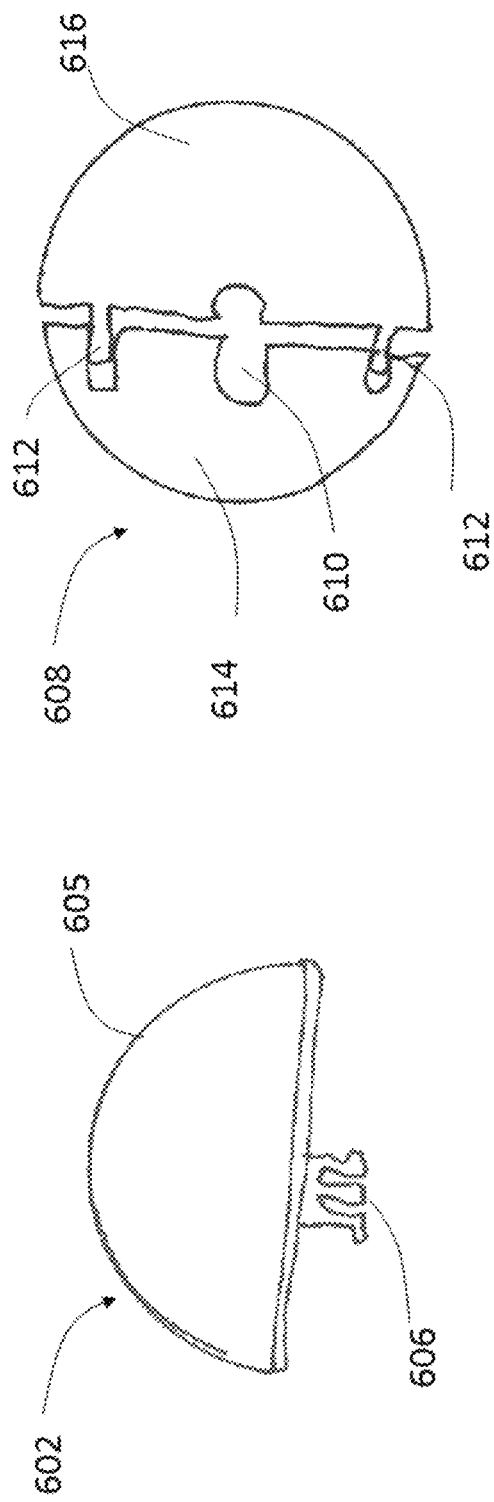
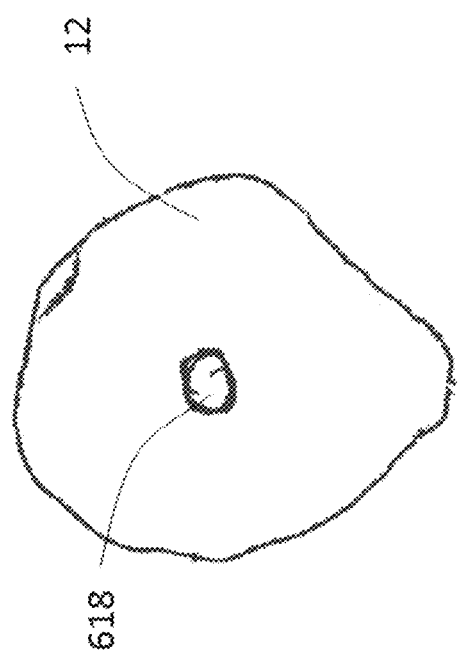

PATELLA TRACKING

CROSS-REFERENCE TO RELATED APPLICATIONS

This application is a continuation of U.S. application Ser. No. 17/975,117, filed Oct. 27, 2022, which is a continuation of U.S. application Ser. No. 16/447,364, filed Jun. 20, 2019, which issued as U.S. Pat. No. 11,510,737 on Nov. 29, 2022, which claims the benefit of the filing date of U.S. Provisional Patent Application No. 62/687,875 filed Jun. 21, 2018, the disclosures of which are hereby incorporated herein by reference in their entirety.

FIELD OF INVENTION

The present invention relates to a surgical system for bone tracking and a method for implant selection utilizing the same, and more particularly to a surgical system for patella tracking and a method for selecting a properly-sized patellar implant utilizing the same.

BACKGROUND OF THE INVENTION

Implants for mobile bones require precise implant sizing and selection to maintain natural bone kinematics. Maintaining natural biomechanics of joints is a key requirement for proper rehabilitation of treated bones. For example, a patellar implant must be properly sized to match a resected patella to ensure proper patellar kinematics during flexion and extension of the patella after implantation. Postoperative patellar kinematics must be similar to a patient's preoperative and/or pre-disease state. Improperly sized patellar implants may alter patellar kinematic resulting in patellar maltracking or other complications.

Selecting a patellar implant based on a single or even a plurality of knee flexion-extension positions may not necessarily ensure proper patellar kinematics over the entire flexion-extension path of a knee joint. The patellar range of motion through extension and flexion involves patellar movement with six degrees of freedom over the course of flexion-extension cycle. Consequently, matching patellar implants based on a single or a plurality of patellar positions may be inadequate to ensure proper patellar kinematics. While anatomically-shaped patellar implants often provide improved knee rehabilitation, proper implant sizing for anatomically-shaped patellar implants can be especially challenging given their complex geometric configuration and range of motion.

Patellar overstuffing, i.e., implanting a patellar implant that results in a patella which is thicker than the natural patella, can decrease passive knee flexion and patellar kinematics during knee flexion. Conversely, patellar understuffing, i.e., implanting a patellar implant that results in a patella which is thinner than the natural patella, may lead to reduced moment arm and subsequently increased quad force requirements during patellar flexion-extension leading to increased contact pressure on the patella. Consequently, proper patella implant selection to ensure that patella is not overstuffed or understuffed is critical for proper patellar kinematics.

Therefore, there exists a need for a surgical system for patella tracking and a method for selecting a patellar implant utilizing the same that overcomes the deficiencies of the prior art.

BRIEF SUMMARY OF THE INVENTION

Disclosed herein are surgical systems for bone tracking and methods for implant selection.

In a first aspect of the present invention an orthopedic surgery system is provided. The orthopedic surgery system may include a first tracker, a second tracker and a patellar tracking system. The first tracker may be configured to contact an unresected patella or a resected patella. The second tracker may be configured to contact a bone. The patellar tracking system may be configured to track the first tracker in contact with the unresected patella in flexion and extension to generate a first path representing a patellar range of motion with reference to the bone. The patellar tracking system may be configured to track the first tracker in contact with the resected patella in flexion and extension to generate a second path representing a patellar trial range of motion with reference to the bone. The resected patella may be in contact with a patellar trial.

In accordance with the first aspect, the patellar tracking system may further include a display to depict the patellar range of motion and the patellar trial range of motion with reference to the bone respectively. The first and second trackers may be detachably secured to the patella and the bone respectively. The patellar tracking system may include a tracking camera to register the positions of the first and second trackers.

Further in accordance with the first aspect, the patellar tracking system may be configured to register the first tracker secured to the unresected patella in at least a first, a second and a third position with reference to the bone to define the first path. The first position may be at patellar flexion, the third positon may be at patellar extension and the second position may be located therebetween.

Still further in accordance with the first aspect, the patellar tracking system may be configured to register the first tracker secured to the resected patella in contact with the patellar trial in at least a first, a second and a third position with the reference to the bone to define the patellar trial range of motion. The first position may be at patellar flexion, the third positon may be at patellar extension and the second position may be located therebetween. The bone may be a femur or tibia.

A second aspect of the present invention is a method for selecting a patellar implant. A method in accordance with this aspect of the invention may include the steps of tracking a location of a point adjacent an unresected patella to generate a first path, resecting the patella and placing a patellar trial on a resected surface of the patella, tracking a location of the point adjacent the resected patella to generate a second path, and displaying and comparing the first path with the second path on a display. The first path may be generated by tracking the location of the point adjacent the unresected patella in flexion and extension. The first path may represent a patellar range of motion with respect to a bone. The second path may be generated by tracking the location of the point adjacent the resected patella with the patellar trial in flexion and extension with respect to the bone.

In accordance with the second aspect, the method may further including the step of selecting a patellar implant. The step of selecting the patellar implant may be based on comparing the first path with the second path on the display such that the difference between the first path and the second path is less than a predetermined value. The predetermined value may be 3 mm.

Further in accordance with the second aspect, the step of tracking the location of the point adjacent the unresected patella in flexion and extension may include the step of placing a first tracker on the patella and a second tracker on the bone and using a patellar tracking system to generate the first path representing the patellar range of motion with reference to the bone. The step of placing the first tracker on the unresected patella may include the step of placing a probe on a check post in contact with the unresected patella. The step of placing a first tracker on the unresected patella may include placing a clamp on the unresected patella. The patellar range of motion may be generated by the step of registering the position of the first tracker on the unresected patella with reference to the bone in at least a first, a second and a third position. The first position may be at patellar flexion, the third positon may be at patellar extension and a second position may be located therebetween.

Still further in accordance with the second aspect, the step of tracking the resected patella in flexion and extension may include the step of placing the first tracker on the resected patella and the second tracker on the bone and using the patellar tracking system to generate the second path representing the patellar trial range of motion with reference to the bone. The patellar trial range of motion may be generated by the step of registering the position of the first tracker on the resected patella with reference to the bone in at least the first, second and third positions.

Still further in accordance with the second aspect, the step of registering may include using a tracking camera to register the positions of the first and second trackers. The step of generating the first path may include using the patellar tracking system to generate the first path between the first, second and third positions of the first tracker placed on the unresected patella to define the patellar range of motion. The step of generating the second path may include using the patellar tracking system to generate the second path between the first, second and third positions of the first tracker placed on the resected patella to define the patellar trial range of motion. The step of displaying and comparing the first path with the second path may include displaying and comparing the first path and the second path on a display screen.

In other aspects, the bone may be a femur or a tibia. The predetermined value may correspond to the reduction or elimination of patellar overstuffing and understuffing Still further in accordance with the second aspect, the method may include the steps of generating virtual models of the patella and of the bone, virtually tracking a location of a point adjacent a virtually resected patella with a virtual patellar trial in flexion and extension to generate a virtual path representing a virtual trial patellar range of motion with respect to the bone, and comparing the first path and the virtual path to identify the patellar trial.

In a third aspect of the present invention, a check post for an orthopedic probe is provided. A check post in accordance with this aspect may include an elongated member and an anti-rotation feature. The elongated member may have a distal end and a proximal end. The distal end may be configured for detachable attachment with a bone or soft tissue at a first location. The proximal end may have first and second recesses to receive an orthopedic tracker. The anti-rotation feature may extend from the proximal end of the elongated member. The anti-rotation feature may include a second elongated member for detachable attachment with the bone or tissue at a second location. The check post may not rotate about the first elongated member when the first elongated member and the anti-rotation feature are attached to the first and second locations respectively of the bone or tissue.

In a fourth aspect of the present invention, a patellar trial assembly is provided. The patellar trial assembly may include an upper bone contacting surface, a lower surface configured to contact a patella or a patellar implant, and a first and second peg extending from the lower surface. The first and second peg may be flexible such that the first and second peg may be pushed towards each other by an external force such that a first distance between distal ends of the first and second peg when the external force is applied is less than a second distance between the distal ends of the first and second peg when the external force is removed.

BRIEF DESCRIPTION OF THE DRAWINGS

A more complete appreciation of the subject matter of the present invention and the various advantages thereof can be realized by reference to the following detailed description, in which reference is made to the following accompanying drawings:

FIG. 11B is a front view of a top portion of the patellar trial assembly of FIG. 11A;

FIG. 11C is a top view of a bottom portion of the patellar trial assembly of FIG. 11A, and FIG. 12 is a top view of a patella with a hole to receive the patellar trial assembly of FIG. 11A.

DETAILED DESCRIPTION

In describing preferred embodiments of the disclosure, reference will be made to directional nomenclature used in describing the human body. It is noted that this nomenclature is used only for convenience and that it is not intended to be limiting with respect to the scope of the invention.

As used herein, when referring to bones or other parts of the body, the term "anterior" means toward the front part or the face and the term "posterior" means toward the back of the body. The term "medial" means toward the midline of the body and the term "lateral" means away from the midline of the body. The term "superior" means closer to the heart and the term "inferior" means more distant from the heart.

Figure 1:
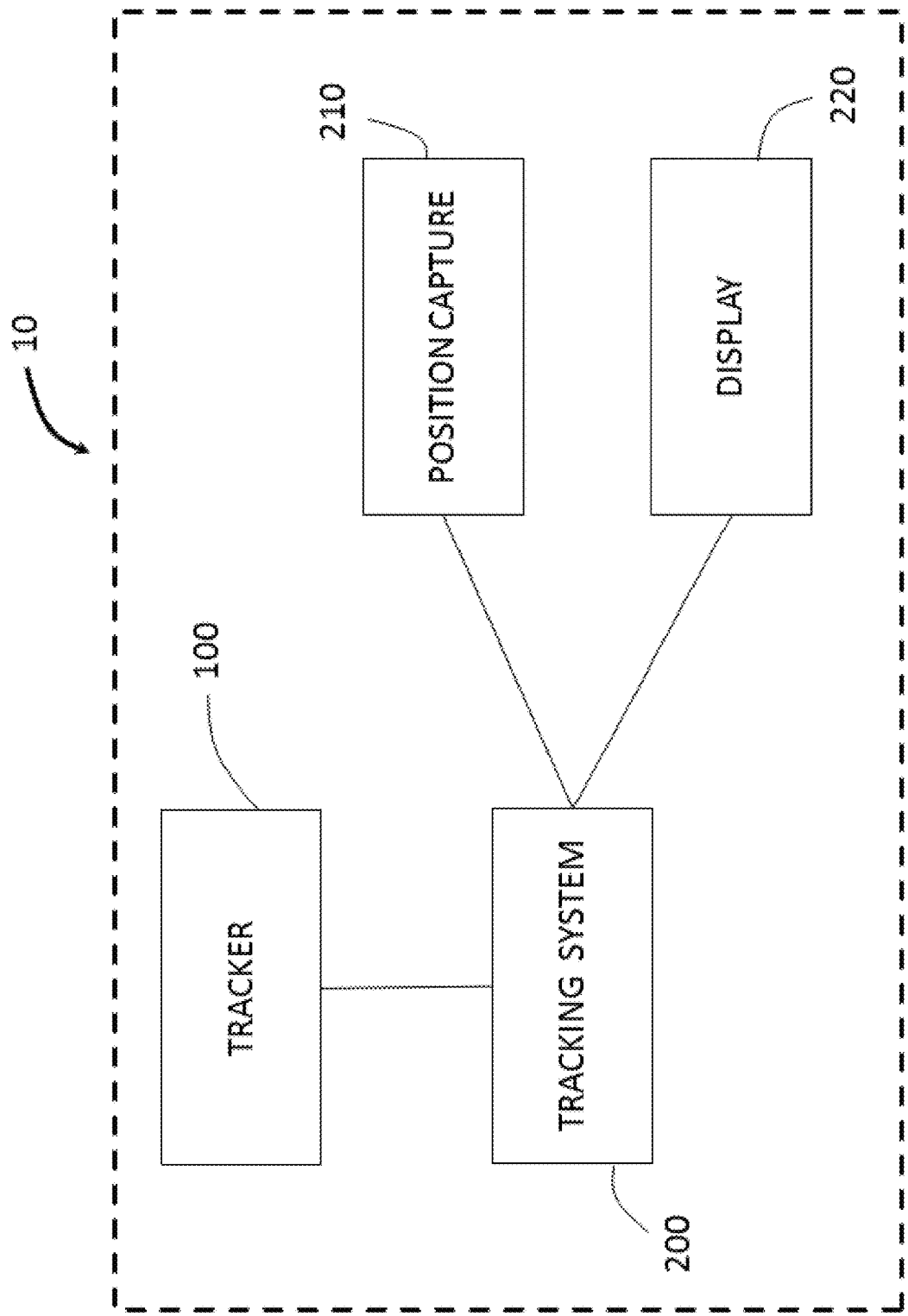
FIG. 1 is a schematic drawing of a surgical system in accordance with an embodiment of the present invention.

Referring to FIG. 1, a first embodiment in accordance with the present invention is a surgical system 10 for bone tracking that includes one or more trackers 100 and a tracking system 200. Tracking system 200 includes a position capturing device 210 and a display 220. While the present description of surgical system 10 relates to tracking a patella, other surgical systems in accordance with the present invention can be configured to track other mobile bones and joints in other embodiments, such as tracking a femur in a hip resurfacing procedure, tracking a humerus in a shoulder surgery, a talar bone during ankle surgery, etc.

Figure 2:
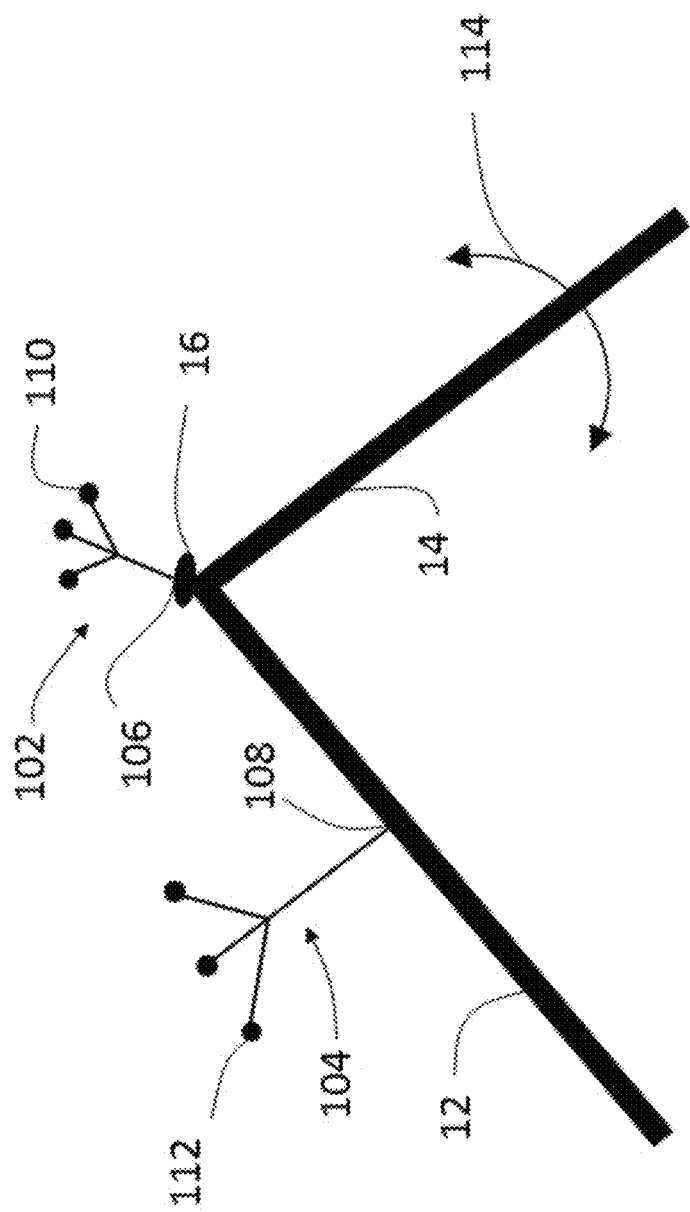
FIG. 2 is a side view schematic depicting trackers of the surgical system of FIG. 1 placed on bone.

FIG. 2 shows a schematic of trackers 100 located on bone for tracking. Trackers 100 include a first tracker 102 and a second tracker 104. First tracker 102 has a distal tip 106 configured to contact bone, such as a patella 16 as shown, and a plurality of fiducials 110 at a proximal end. Fiducials 110 are spherical-shaped markers configured to be identified by position capturing device 210. The number, shape and properties of markers can be varied depending on the type of the position capturing device being utilized and the nature of bone being tracked. For example, radiopaque markers can be used with an X-ray or a CT scan position capturing device, whereas markers with reflectors can be used with a camera position capturing device. Second tracker 104 has a distal tip 108 configured to contact bone, such as a femur 12 as shown, and a plurality of fiducials 112 at a proximal end. Distal tip 108 and fiducials 112 are similar to distal tip 106 and fiducials 110 of first tracker 102.

As shown in FIG. 2, distal tip 106 of first tracker 102 is placed in contact with patella 16 and distal tip 108 of second tracker 104 is placed in contact with femur 12. The distal tip of the tracker can be configured to be firmly secured and anchored on the bone requiring no manual support, or it can be configured to allow an operator to manually hold the tracker in place during tracking. A clamp or other suitable device (not shown) can be used to secure patella 16 prior to placing first tracker 102. A navigated patella clamp with a tracker may be used to intraoperatively inform the surgeon where to place the clamp on the patella in the manner disclosed in U.S. patent application Ser. No. 15/087,202, the disclosure of which is hereby incorporated by reference herein. Second tracker 104 serves as a reference to track patellar position during flexion-extension, and consequently can be placed on tibia 14 instead of femur 12 to obtain similar results. While the distal tips of trackers 102, 104 are placed directly on bone in this embodiment, in other embodiments distal tips can be placed on a check post affixed to the bone as more fully described below.

Second tracker 104 is anchored on femur 12 to provide a reference point to accurately track the location of distal tip 106 of first tracker 102 as tibia 14 is moved between flexion and extension indicated by direction 114. Tracking the location and movement of fiducials 110, 112 through flexion and extension allows tracking system 200 to accurately record and display precise position and orientation of distal tip 106, and therefore, patella 16 through knee flexion-extension cycle. While patellar tracking is disclosed in this embodiment, other embodiments may track other mobile bones using surgical system 10 as indicated above.

Figure 3:
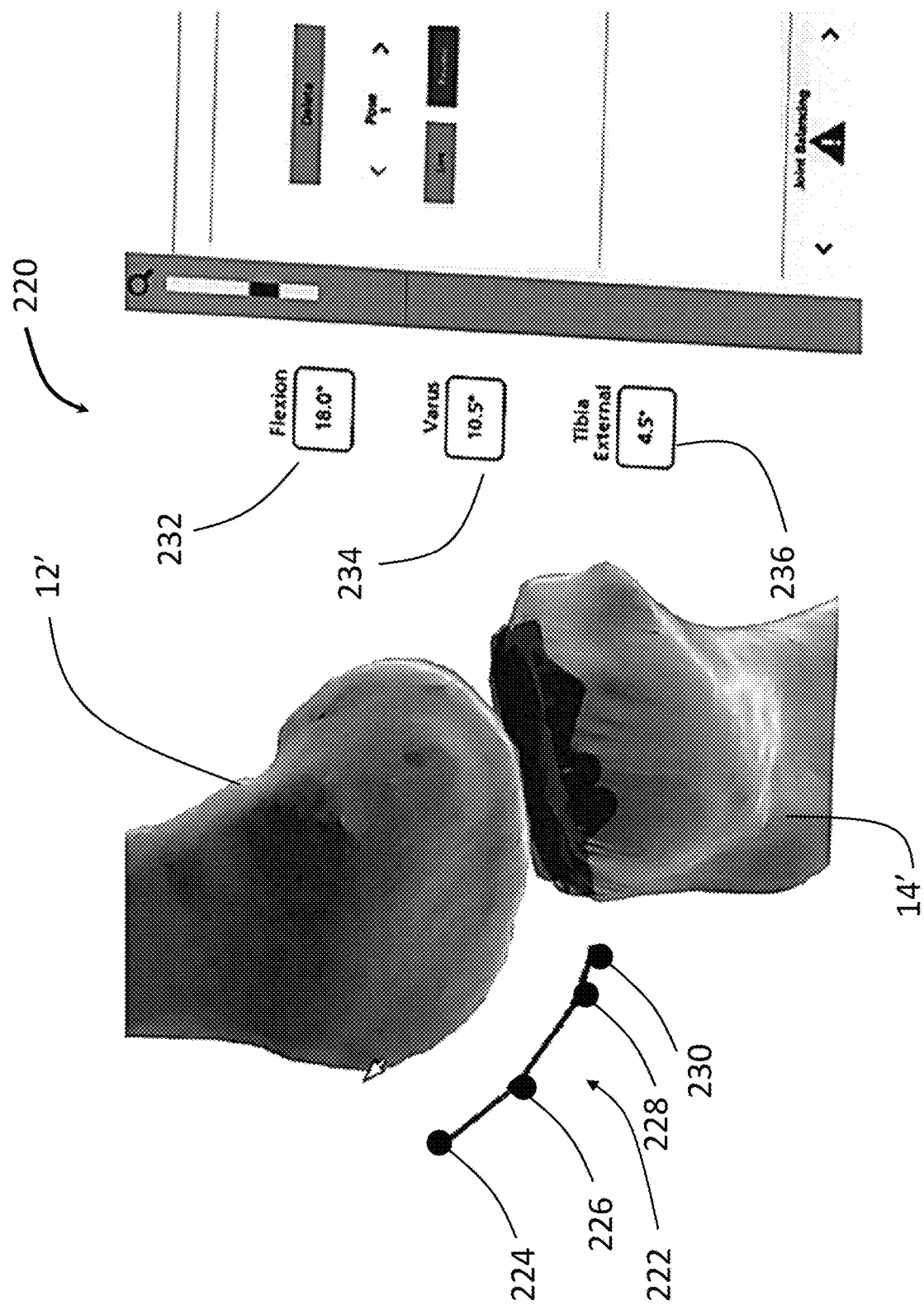
FIG. 3 is a graphical representation of a femur and tibia showing a first path defined by the trackers of FIG. 2 on a display.
Figure 4:
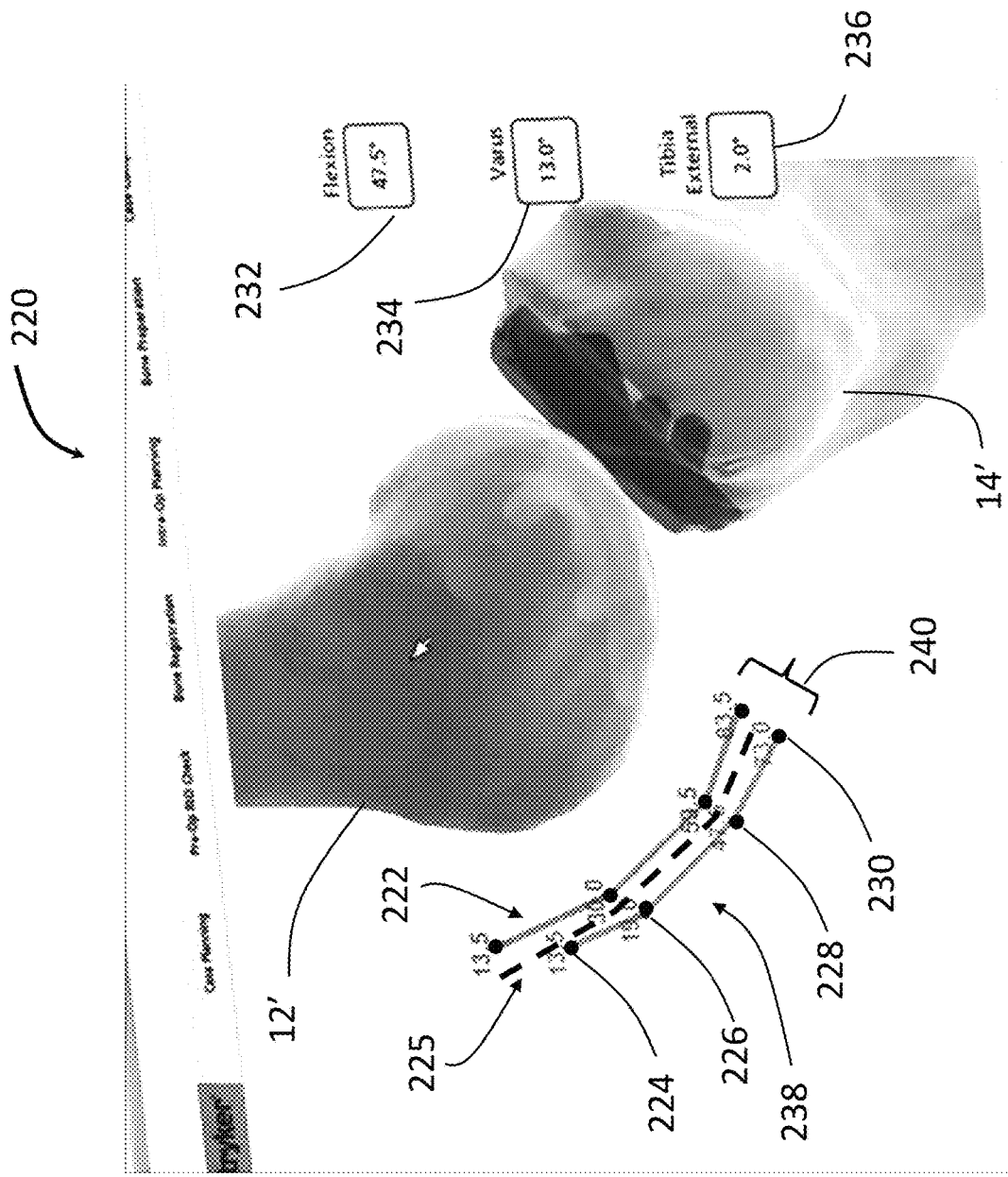
FIG. 4 is a graphical representation of a femur and tibia showing a second path defined by the trackers of FIG. 2 on the display.

Referring now to FIGS. 3 and 4, there is shown a display 220 with patellar tracking information captured by image capture device 210. Display 220 depicts virtual bone models of femur 12' and tibia 14'. The virtual bone models can be preoperatively captured and displayed on display 220, or can be intraoperatively captured during bone tracking. As shown in FIG. 3, distal tip 106 placed on an unresected patella 16 is tracked at four different positions 224, 226, 228 and 230 of unresected patella 116 as it moves from flexion to extension. A flexion angle indicator 232 allows an operator to identify the precise angle of flexion for each of these positions. Display 220 generates a first path 220 defined by positions 224, 226, 228 and 230. First path 220 identifies the location of the patella surface at distal tip 106 of first tracker 102 along flexion and extension of unresected patella 16 and depicts the preoperative patellar range of motion during the flexion-extension cycle. Other locations on unresected patella 16, which are not contacted by the distal tip, can also be derived from distal tip 106 location and used to generate first path 220. Other parameters of the patellofemoral joint shown in FIG. 2 can also be shown on display 220 to record and analyze patellar movement during flexion and extension. For example, varus-valgus angulation 234 with anteroposterior translation around an anteroposterior axis and a tibia external angle 236 are shown in display 220 of FIG. 3.

With this information, the next step in the procedure is the resection of the patella. Depending on the geometry of first path 222, surgical system 10 and/or an operator can determine the characteristics of the patient's patellar range of motion and other relevant metrics to calculate or optimize the patellar resection depth. Patella resection is subsequently performed utilizing this information.

A second path 238 is defined by positions 224, 226, 228 and 230 with distal tip 106 on a resected patella with a patellar trial as shown in FIG. 4. Second path 238 is defined by tracking patellar position at a plurality of locations during patellar flexion and extension as first path 222 and depicts a patellar trial range of motion. While the patella itself is not shown, the patella during this step includes an implant having a particular thickness anchored to the resected surface. This step therefore trials the location of an exterior portion of the modified patella through flexion-extension. The plurality of locations tracked for second path 238 can be generally the same as the locations used to generate first path 222, which allows for comparison of the data from the unresected and resected procedures. An optimal path 225 representing the desired patellar path is also displayed to assist the surgeon in selecting the appropriate patellar implant. Optimal path 225 can be determined by utilizing a contralateral healthy patellar range of motion, a patellar range of motion database or other similar methods. A contralateral healthy patellar range of motion can be obtained by utilizing surgical system 10. As shown here, positions 224, 226, 228 and 230 correspond to patellar flexion angles of 13.5°, 19.0°, 47.5° and 73.0°, respectively.

First path 222 is overlaid on display 220 for visual comparison between the preoperative patellar range of motion and the patellar trial range of motion. A difference 240 between first path 222 and second path 238 depicts whether there may be patellar understuffing or overstuffing. As shown in FIG. 4, second path 238 representing the patellar trial range of motion is farther away from first path 222 representing the preoperative patellar trial range of motion with reference to patellofemoral joint. Hence, the patellar trial range of motion depicted by second path 238 represents an overstuffed patella. Difference 240 denotes the level of overstuffing. If second path 238 was closer to the patellofemoral joint than first path 222, second path 238 would represent an understuffed patella. The magnitude of difference between first and second paths denotes the level of overstuffing/understuffing and/or improper alignment.

Figure 5:
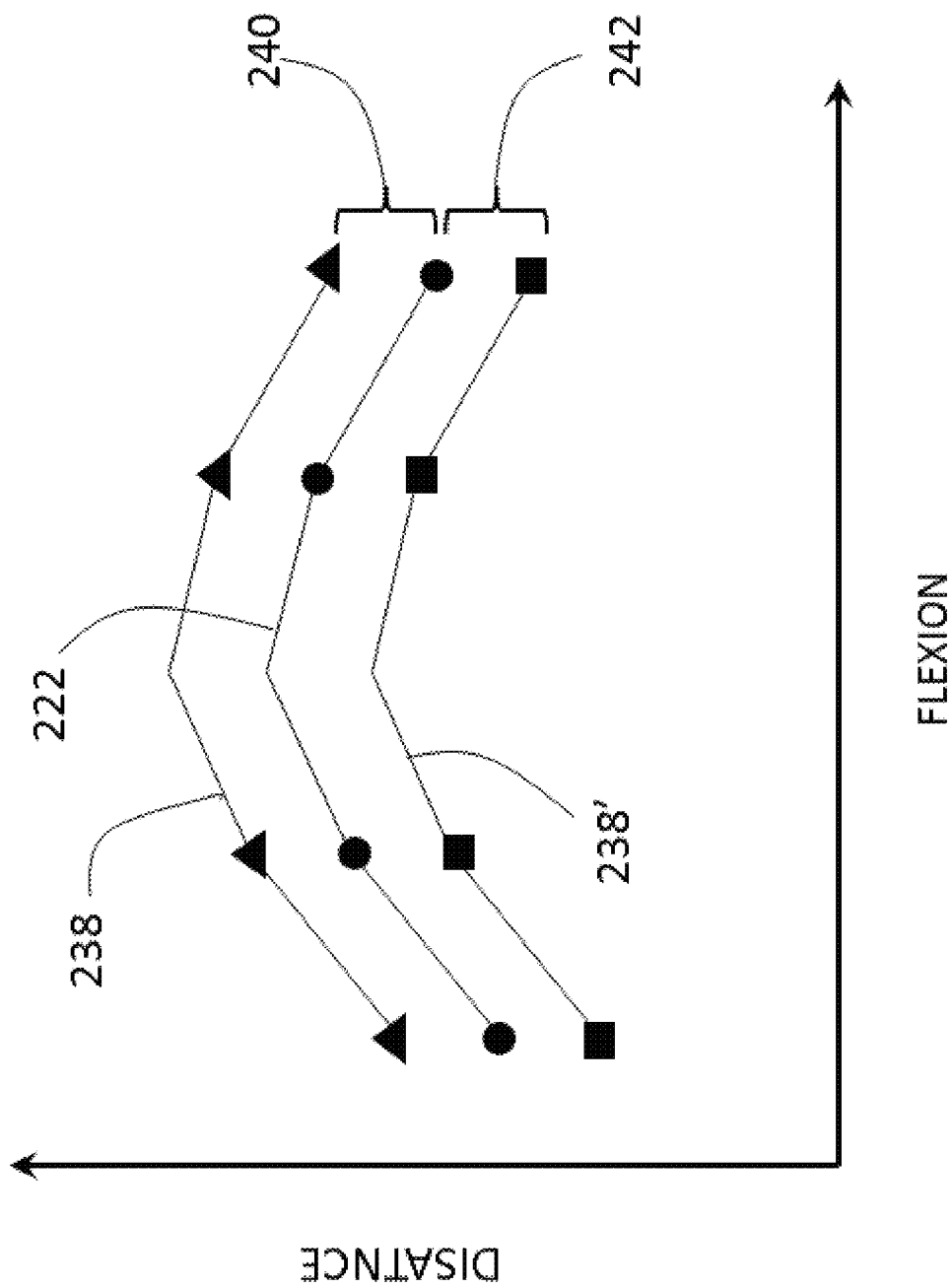
FIG. 5 is a graph showing patellar understuffing and overstuffing limits during flexion and extension.
Figure 10:
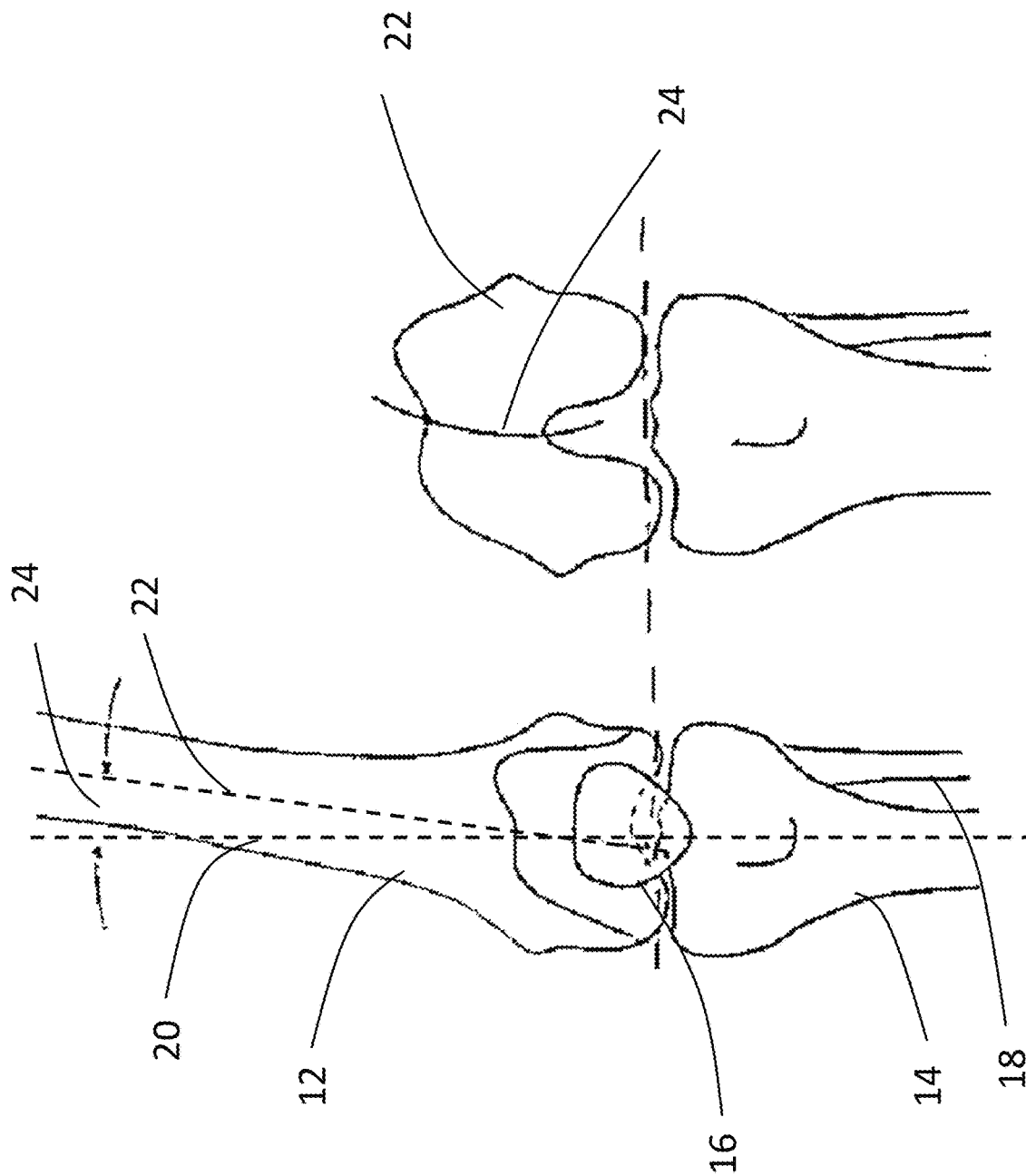
FIG. 10 shows front schematic views of a patellofemoral joint.

FIG. 5 shows a graph depicting preoperative patellar range of motion 222 and patellar trial ranges of motion 238 and 238' during patellar flexion-extension cycle. In this example, preoperative patellar range of motion is assumed to be identical to optimal path 225—i.e., the preoperative patellar range of motion represent the optimal patellar range of motion. Patellar trial range of motion 238 represents an overstuffed patella whereas patellar trial range of motion 238' represents an understuffed patella. Patellar or patellar trial positions recorded at four locations are shown in this graph, but other embodiments may have fewer or greater number of recorded positions depending on the level of tracking accuracy required. Patellar overstuffing 240 and under patellar understuffing 242 limits are depicted in FIG. 5. By way of example only and not intended to be limiting in scope, maximum patellar overstuffing and understuffing limits should be preferably less than 3 mm to maintain the natural patellofemoral kinematics. The limits being calculated as the difference between two identical tracking positions—i.e., flexion angle, measured along a line joining the tracking positions. Correspondingly, patellar implant selection and patellar resection depths are determined based on these limits to prevent patellar overstuffing and understuffing. While patellar tracking for patellar overstuffing and understuffing is described in this embodiment, surgical system 10 can be used to track and analyze other patellofemoral kinematic metrics such as varus-valgus angulation, internal-external rotation of the patella, deviation of patellar contact surface from Whiteside's Line 24 as shown in FIG. 10, etc.

Figure 6:
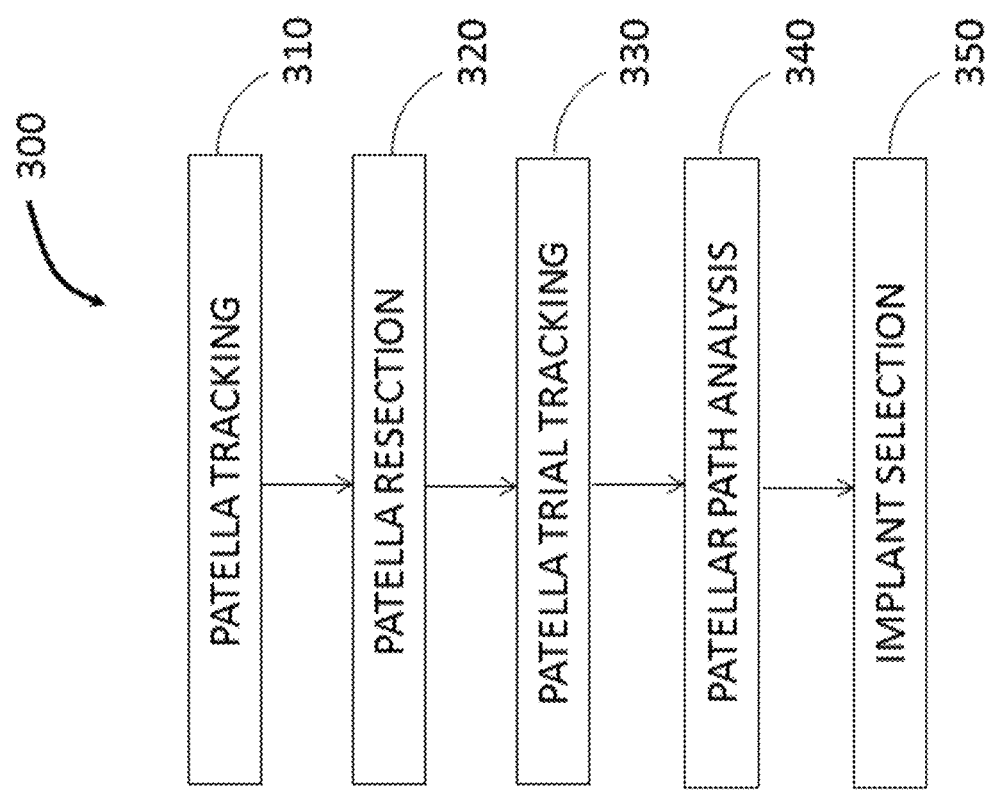
FIG. 6 is a flowchart showing the steps for selecting a patellar implant utilizing a patellar trial in accordance with another embodiment of the present invention.

Referring now to FIG. 6, there is shown a flowchart depicting a method 300 for patellar implant selection according to another embodiment of the present invention. In step 300, a preoperative patellar range of motion in flexion and extension is tracked and displayed on display 220. As described above, first tracker 102 is placed in contact with unresected patella 16 and second tracker 104 is placed on femur 12 or tibia 14 to provide a reference point. First tracker 102 can also be placed on a check post that is in contact with bone as more fully described below. A clamp or other suitable device can be placed on patella 16 to facilitate placement of first tracker 102. Patella 16 is then moved from flexion to extension to allow image capture device 210 to record patella position at a plurality of locations and display the same as first path 222 on display 220. The number of locations to record patellar positions can be varied depending on the accuracy required for the patellar range of motion.

In step 320, a surgeon performs a patellar resection based on a predetermined resection depth. Resection depth can be preoperatively determined by evaluating medical images of the patella or intraoperatively determined by utilizing tacking system 200. A surgeon then places a suitable patellar trial on the resected patella and performs step 330. In step 330, first tracker 102 is placed on the resected patella with the patellar trial and patellar positions at a plurality of positions during flexion-extension are recorded and displayed on display 200 to defined second path 238. As more fully described above, second path 238 represents the patellar trial range of motion for that particularly dimensioned trial implant. In step 340, first path 222 and second path 238 are displayed on display 220 and analyzed to determined patellar overstuffing or patellar understuffing. If the selected patellar trial results in overstuffing in excess of predetermined tolerance limits, the surgeon can select a thinner patellar trial and repeat step 330. Similarly, if the selected patellar trial results in understuffing, the surgeon can select a thicker patellar trial and repeat step 330. Once a suitable patellar trial is identified and verified to simulate natural or a desired patellar kinematics, a corresponding patellar implant is selected in step 350 and then implanted. Final testing can be done to ensure proper kinematics of the permanent implant.

Figure 7:
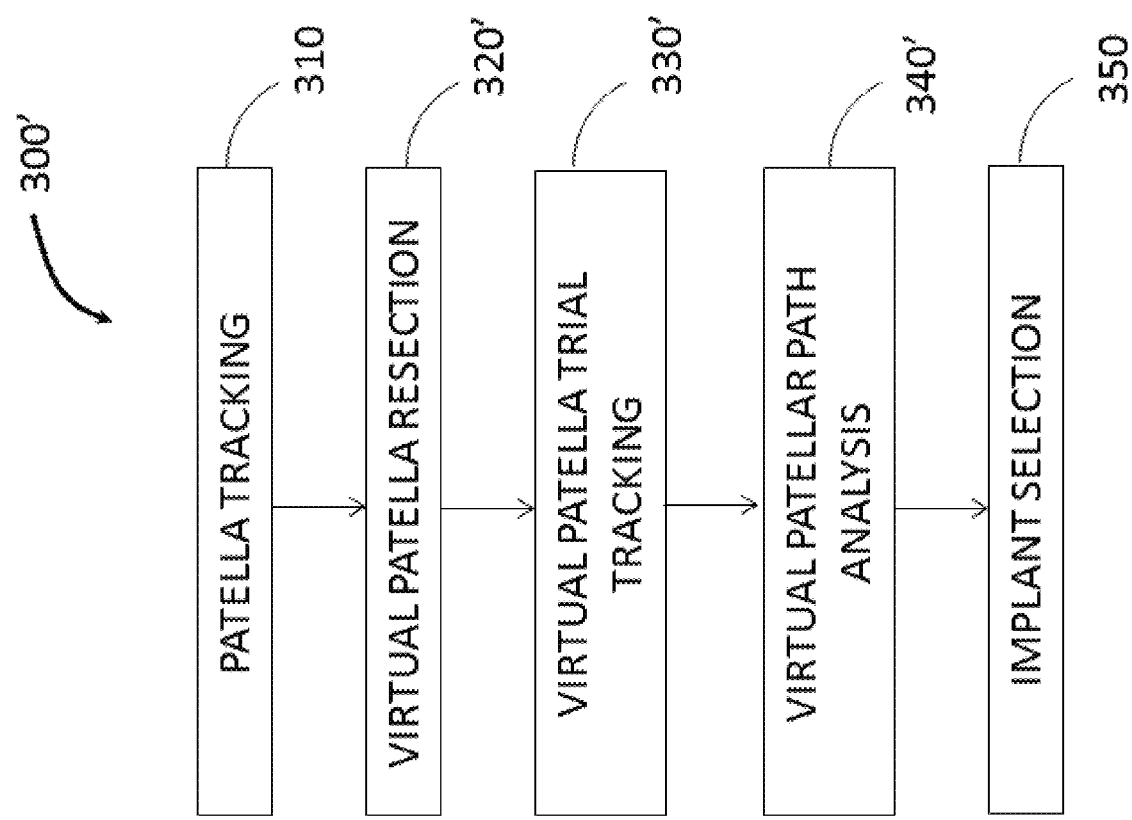
FIG. 7 is a flowchart showing the steps for selecting a patellar implant utilizing a virtual patellar trial in accordance with yet another embodiment of the present invention.

FIG. 7 shows a method 300' for patellar selection utilizing a virtual patellar trial according to another embodiment of the present invention. Method 300' is similar to method 300 and includes step 310 to track and record the preoperative patellar range of motion as described above. However, once the preoperative patellar range of motion is determined, surgical system 10 can virtually determine a patellar resection depth in step 320'. The virtual resection depth can be determined by analyzing imaging of the patellofemoral joint and patient-specific requirements. After a virtual resection depth is determined, a virtual patellar trial tracking 330' using a virtual patellar trial is performed by surgical system 10. A virtual patellar path analysis with reference to the preoperative patellar range of motion is performed in step 340' to identify and select the required patellar implant by surgical system 10. Therefore, method 300' provides a surgeon with the resection depth and patellar implant selection based on patella tracking step 310. Method 300' will aid in various patellar preparation steps such as attachment options for securing a patellar trial to a resected patella, placement of a cutting jig to perform patella resection, etc.

Figure 8:
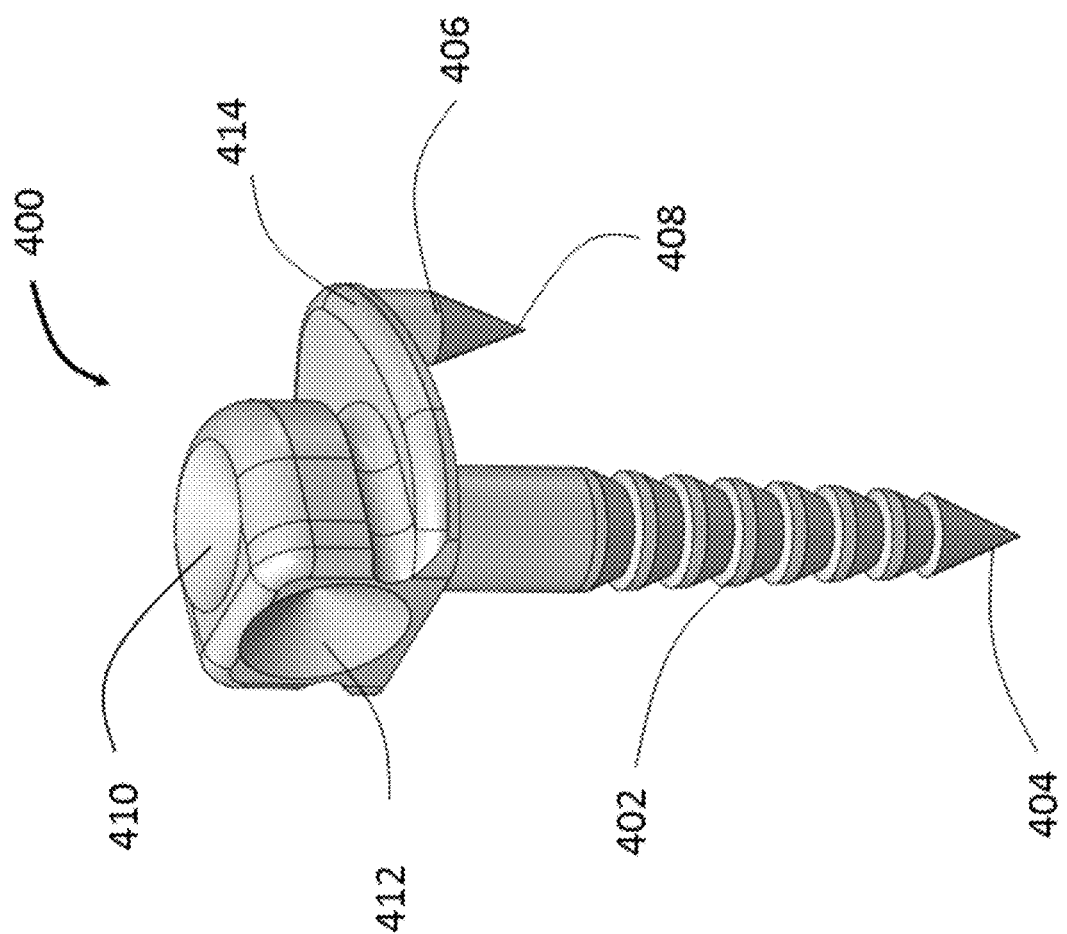
FIG. 8 is a perspective view of a check post according to another embodiment of the present invention.

Referring now to FIG. 8, there is shown a check post 400 according to another embodiment of the present invention. Check post 400 is configured to be securely positioned on a mobile body portion such as skin or bone, i.e. the patella, to allow for recording the contacted body portion in six degrees of freedom via the trackers described above. For example, check post 400 can be placed on a patella to record extension with mediolateral translation around a mediolateral axis, varus-valgus angulation with anteroposterior translation around an anteroposterior axis, and internal and external rotation with superoinferior translation around a superoinferior axis.

Check post 400 includes a first elongated member 402 with a first distal tip 404. Distal tip 404 is shaped to engage with bone or skin and securely affix check post 400 to the same. A predrilled bore on bone can aid in securing check post 400 to the bone. The predrilled bore can also serve as the anchoring receptacle to receive the patellar implant in order to minimize patellar resection. Grooves or ridges along elongated member 402 are provided to further enhance the connection between check post 400 and bone or skin. An anti-rotation feature 414 including a second elongated member 406 with a second distal tip 408 is provided. Second distal tip 408 is also configured to engage firmly with bone or skin such that check post 400 does not rotate. For example, check post 400 will not rotate about a longitudinal axis defined by elongated member 402 during patellar extension and flexion when distal tips 404, 408 are secured to a patella. A proximal end of check post 400 includes a first recess 410 at a proximal end and a second recess 412 normal to first recess 410. Recesses 410 and 412 are shaped to receive and hold distal tips of trackers during patellar flexion and extension. For example, distal tips 106 and 108 of the first and second trackers shown in FIG. 2 can be placed in recesses 410 or 412.

Check post 400 can be utilized in method 300 for patellar implant selection described above. Check post 400 can be anchored to unresected patella 16 by securing distal tip 404 in the patella. A predrilled bore on unresected patella 16 can also be used to facilitate anchoring check post 400 to patella 16. Distal tip 106 can now be placed in recess 410 or recess 412. Recess 410 and 412 are configured to receive and hold the distal tip through the patellar tracking by allowing the distal tip to rotate within the recess during flexion-extension cycles without breaking contact between the distal tip and the recess. Check post 400 can be similarly used for performing the step of patellar trial tracking 330.

Figure 9A:
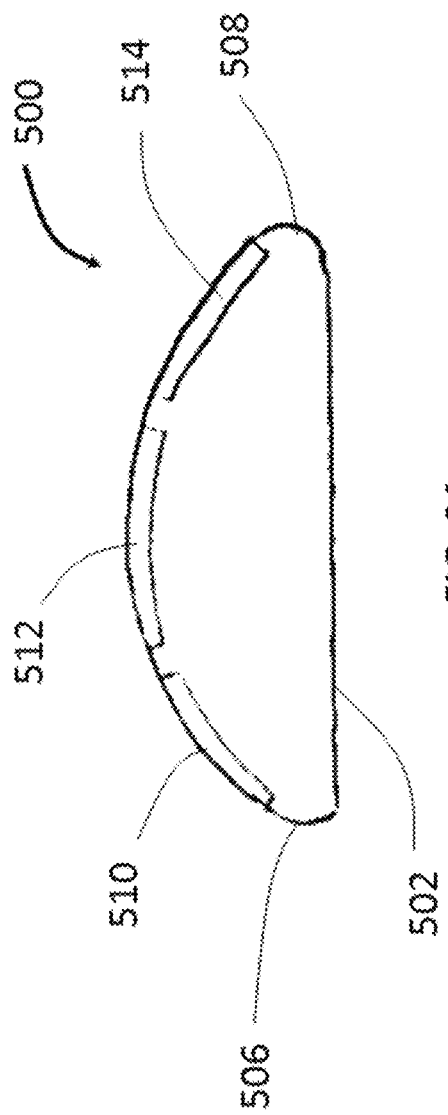
FIG. 9A is a side view of a patellar trial according to another embodiment of the present invention.
Figure 9B:
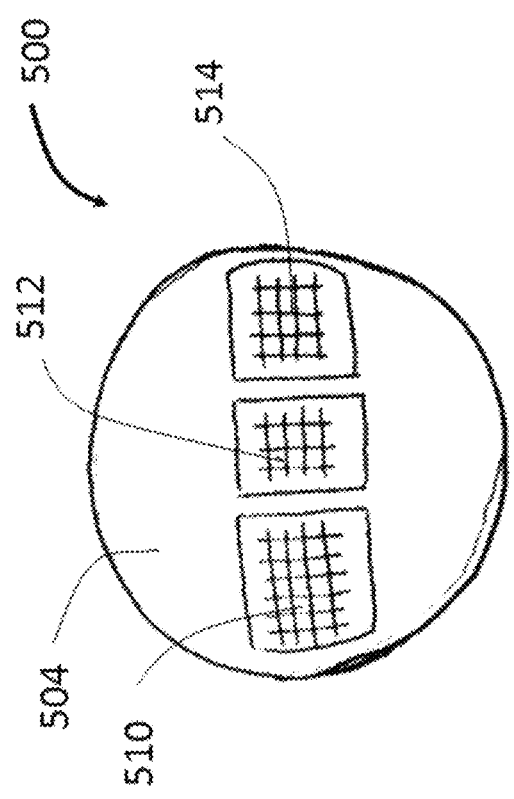
FIG. 9B is a top view of the patellar trial of FIG. 9A.

FIGS. 9A and 9B show a patellar trial 500 according to another embodiment of the present invention. Patellar trial 500 includes a patella contacting surface 502, a femur contacting surface 504 bounded by a medial side 506 and a lateral side 508. Femur contacting surface 504 includes a medial sensor 510, a central sensor 512 and a lateral sensor 514. Sensors can be mechanical, electrical, acoustical sensors or any combination thereof configured to detect patellofemoral kinematics. For example, sensors can be configured to track medial-lateral deflection of a patella 16 shown in FIG. 10. Contact surface area and contact pressure can be detected by sensors 510, 512 and 514 during flexion and extension of patellar trial 500 in contact with a resected patella (not shown) and/or other anatomical landmarks such as a 18 fibula, etc. shown in FIG. 10. This data can be transferred to a display device and compared with patellar tracking data obtained from a contralateral patella or a database containing patellar tracking information. Sensors 510, 512, and 514 can be used to determine a quadriceps angle ("Q-angle") 24 defined as the angle between an anatomical axis 22 and a mechanical axis 20 of patella 16. Q-angles outside the prescribed range can indicate a risk of chondramalacia patella, patella alta or mal tracking of the patella. A surgeon can confirm proper patellar implant sizing by analyzing the feedback from patellar trial 500 to ensure that Q-angle 24 is within the desired range. While three sensors are shown here, other embodiments can have a single or a plurality of sensors disposed on and within patellar trial 500 to aid in patellofemoral procedures.

Figure 11A:
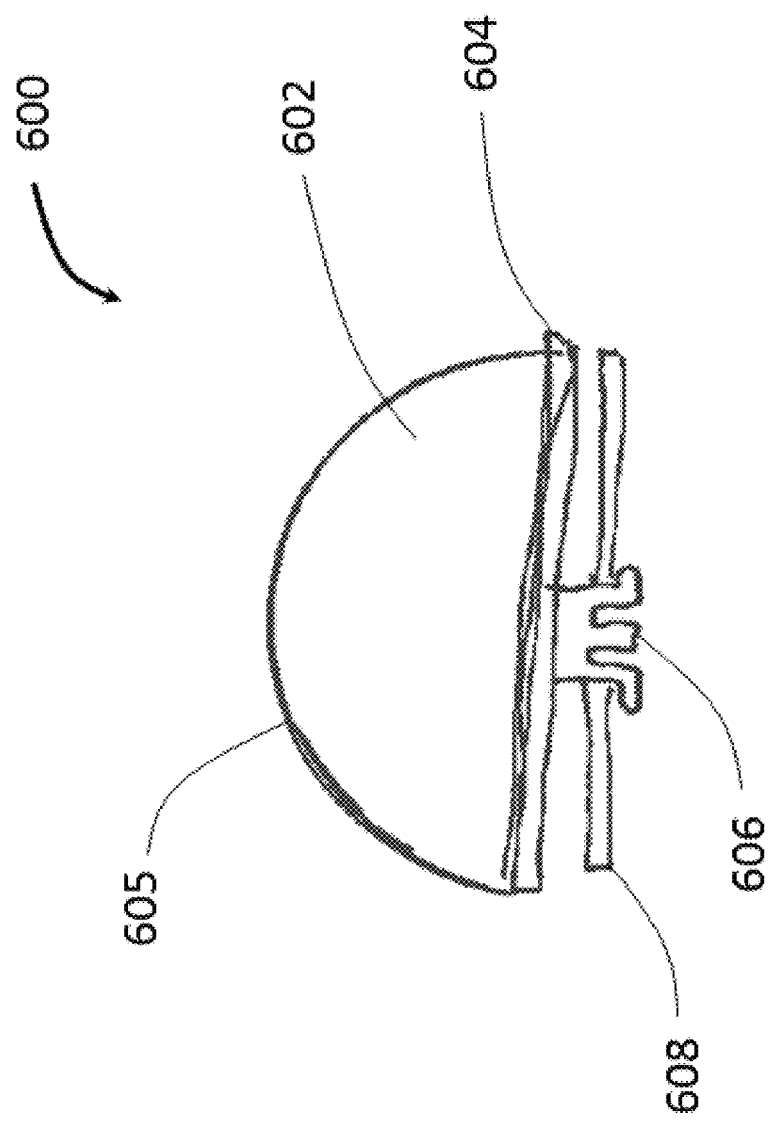
FIG. 11A is a front view of a patellar trial assembly according to another embodiment of the present invention.

Referring now to FIGS. 11A, 11B and 11C, there is shown a patellar trial assembly 600 according to another embodiment of the present invention. Patellar trial assembly 600 includes a top portion 602 and a bottom portion 608. Top portion 608 includes a femur contacting surface 605 and a bottom surface 604. Surface 605 is made of a polymeric material or other suitable material to allow sliding contact with a femur. Bottom surface 604 can be metallic or other suitably hard material. A peg 606 extends from bottom surface 604 and has three prongs. The outer prongs have lateral and medial extensions as best shown in FIGS. 11A and 11B. The prongs of peg 606 are configured to be flexible to allow the outer pongs to be compressed towards the center prong. In other embodiments, the prongs can be circumferentially spaced in a circular orientation.

Bottom portion 608 includes a first surface 614 and a second surface 616 as shown in FIG. 11C. A slot 610 is centrally located between first surface 614 and second surface 616. Springs 612 disposed on either side of slot 610 bias first surface 614 away from second surface 616. Peg 606 is sized to fit through slot 610 as shown in FIG. 11A. An operator can squeeze or push first surface 614 and second surface toward each other to compress peg 606. The compressed peg 606 can then be placed into a predrilled hole 618 on patella 12 shown in FIG. 12. Upon release of the compressive force on bottom portion 608, first surface 614 and second surface 616 are pushed apart by springs 612 and thereby allowing the outer prongs of peg 606 to expand and contact the sides of hole 618. Hole 618 is configured to be slightly smaller than uncompressed peg 616 such that patellar trial assembly 600 is now secured to patella 12. To detach patellar trial assembly 600 from patella 12, an operator can compress peg 606 by squeezing bottom portion 608 in the same manner as described above and removing patellar trial assembly 600 from the patella. While a flexible peg attachment mechanism with a compressive plate is described here, other embodiments can have different attachment mechanisms such as a peg expander, a peg with a threaded end to engage a corresponding threaded hole in the patella, a vacuum attachment mechanism, etc. to facilitate convenient attachment and detachment of patellar trials.

Furthermore, although the invention disclosed herein has been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the paragraphs below. Moreover, the foregoing disclosure should be taken by way of illustration rather than by way of limitation as the present invention is defined in the examples of the numbered paragraphs, which describe features in accordance with various embodiments of the invention, set forth in the paragraphs below.

The invention claimed is:

1. A method for selecting a patellar implant comprising:
displaying a first path representing a desired patellar range of motion with respect to a bone on a display;
resecting a patella and placing a patellar trial on a resected surface of the patella;
tracking a reference point adjacent the bone with the patellar trial in flexion and extension;
generating a second path representing a patellar trial range of motion with respect to the bone on the display; and
displaying and comparing the first path with the second path on the display.

2. The method of claim 1, wherein the step of displaying the first path includes a step of generating the first path from a patellar range of motion database.

3. The method of claim 1, wherein the step of displaying the first path includes a step of generating the first path from a contralateral healthy patellar range of motion.

4. The method of claim 3, wherein the step of displaying the first path includes a step of tracking a location of a point adjacent a contralateral healthy unresected patella in flexion and extension.

5. The method of claim 1, further including the step of selecting a patellar implant.

6. The method of claim 5, wherein the step of selecting the patellar implant is based on comparing the first path with the second path on the display such that a difference between the first path and the second path is less than a predetermined value.

7. The method of claim 1, wherein the step of tracking the reference point adjacent the bone in flexion and extension includes placing a tracker adjacent a femur and using a patellar tracking system to generate the second path representing the patellar range of motion with reference to the bone.

8. The method of claim 7, wherein the step of placing the tracker adjacent the femur includes the step of placing a probe on a check post in contact with the femur.

9. The method of claim 8, wherein the patellar trial range of motion is generated by the step of registering a position of the tracker adjacent the bone in at least a first, a second and a third position, the first position being at patellar flexion, the third position being at patellar extension and a second position being located therebetween.

10. The method of claim 9, wherein the step of registering includes using a tracking camera to register the positions of the tracker.

11. The method of claim 10, wherein the step of generating the second path includes using the patellar tracking system to generate the second path between the first, second and third positions of the tracker placed adjacent the resected patella to define the patellar trial range of motion.

12. The method of claim 11, wherein the step of displaying and comparing the first path with the second path includes displaying and comparing the first path and the second path on a display screen.

13. A method for selecting a patellar implant comprising:
displaying a first path representing a desired patellar range of motion with respect to a bone on a display;
generating virtual models of a patella and of the bone;
virtually tracking a location of a point adjacent the bone with a virtual patellar trial in flexion and extension to generate a virtual path representing a virtual trial patellar range of motion with respect to the bone; and
displaying and comparing the first path with the virtual path on the display.

14. The method of claim 13, further including the step of selecting a patellar implant based on comparing a difference between the first path and the virtual path.

15. A method for patella tracking comprising:
displaying a first path representing a desired patellar range of motion with respect to a bone on a display;
tracking a reference point adjacent the bone in flexion and extension, the reference point being indicative of a relative position of a patella;
generating a second path representing a patellar range of motion of the patella with respect to the bone on the display; and
displaying and comparing the first path with the second path on the display.

16. The method of claim 15, wherein the step of displaying the first path includes a step of generating the first path from a patellar range of motion database.

17. The method of claim 15, wherein the step of displaying the first path includes a step of generating the first path from a contralateral healthy patellar range of motion.

18. The method of claim 17, wherein the step of displaying the first path includes a step of tracking a location of a point adjacent a contralateral healthy unresected patella in flexion and extension.

19. The method of claim 15, further including the step of evaluating a difference between the first path and the second path to identify patella kinematics.

20. The method of claim 15, wherein the bone is a femur.

* * * * *